United States Patent
Weckstrom et al.

[11] Patent Number: 6,041,247
[45] Date of Patent: Mar. 21, 2000

[54] NON-INVASIVE OPTICAL MEASURING SENSOR AND MEASURING METHOD

[75] Inventors: Kurt P. Weckstrom, Espoo; Kimmo J. Ristolainen, Helsinki, both of Finland

[73] Assignee: Instrumentarium Corp, Helsinki, Finland

[21] Appl. No.: 09/208,171

[22] Filed: Dec. 9, 1998

Related U.S. Application Data

[63] Continuation-in-part of application No. 08/757,270, Nov. 29, 1996, abandoned.

[30] Foreign Application Priority Data

Nov. 29, 1995 [FI] Finland ..................................... 955758

[51] Int. Cl.⁷ ....................................................... A61B 5/00
[52] U.S. Cl. ............................................................. 600/323
[58] Field of Search ................................... 600/310, 311, 600/322, 323, 325, 327, 332, 337, 338, 339, 341, 342; 362/32, 341; 250/227.28, 227.29, 227.31

[56] References Cited

U.S. PATENT DOCUMENTS

| | | |
|---|---|---|
| 3,123,066 | 3/1964 | Brumley . |
| 5,103,829 | 4/1992 | Suzuki et al. . |
| 5,279,295 | 1/1994 | Martens et al. . |

FOREIGN PATENT DOCUMENTS

| | | |
|---|---|---|
| 25 17 129 | 6/1976 | Germany . |
| 53-26437 | 8/1978 | Japan . |
| 90/07905 | 7/1990 | WIPO . |
| 92/21281 | 12/1992 | WIPO . |
| 96/37259 | 11/1996 | WIPO . |

OTHER PUBLICATIONS

Spectrophotometric Monitoring of Arterial Oxygen Saturation in the Fingertip, I. Yoshiya et al. Medical & Biological Engineering & Computing, Jan. 1980, pp. 27–32.

*Primary Examiner*—Eric F. Winakur
*Attorney, Agent, or Firm*—Andrus, Sceales, Starke & Sawall

[57] ABSTRACT

An optical sensor for non-invasively measuring the content or composition of one or more chemical components within especially a living tissue of a body portion. Radiation sources (38), emit measuring radiation with at least two wavelengths to a portion (6) of the body of a patient. A detector (37) receives the measuring radiation having passed through said body portion of a patient and converts same to electric form. At least one radiation transfer section is located between either the radiation sources or respectively the detectors and the external surface (50) of the body portion of a patient. The radiation transfer section includes measuring-radiation transmitting ends. An outer end (16, 26) facing the external body surface (50) has a surface area which is generally larger than the surface area of an inner end (13a; 19a) facing any given radiation sources or respectively detectors. A measuring-radiation diffusely reflecting surface (14, 17) is positioned between the ends. The sensor may comprise a pulse oximeter sensor.

41 Claims, 4 Drawing Sheets

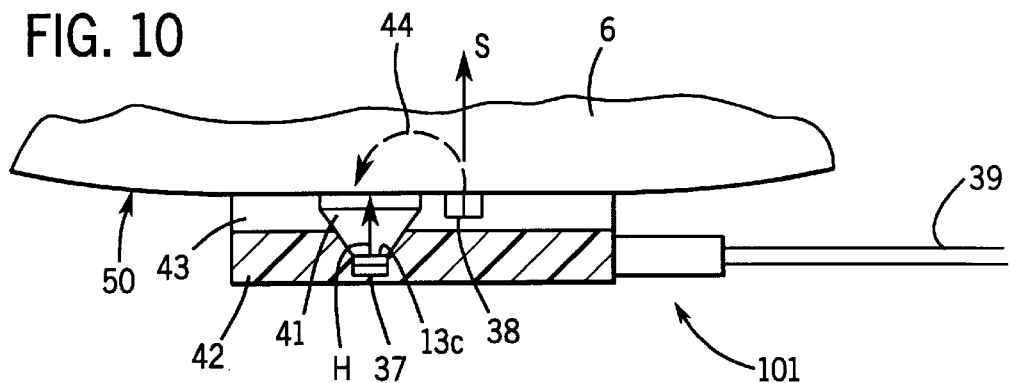
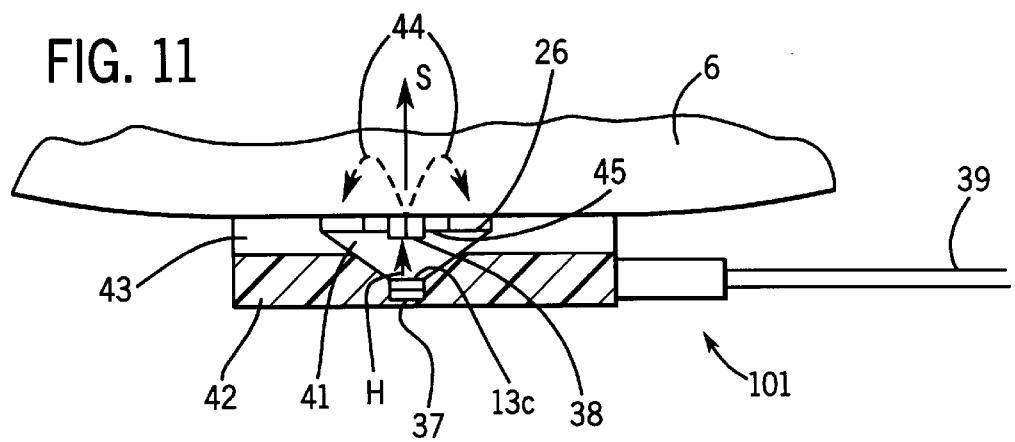
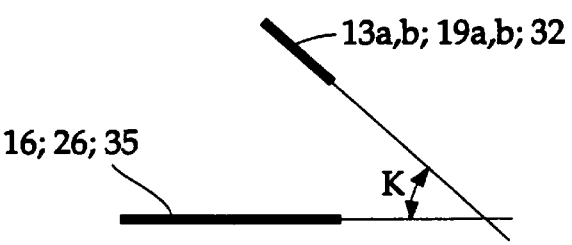
FIG. 12
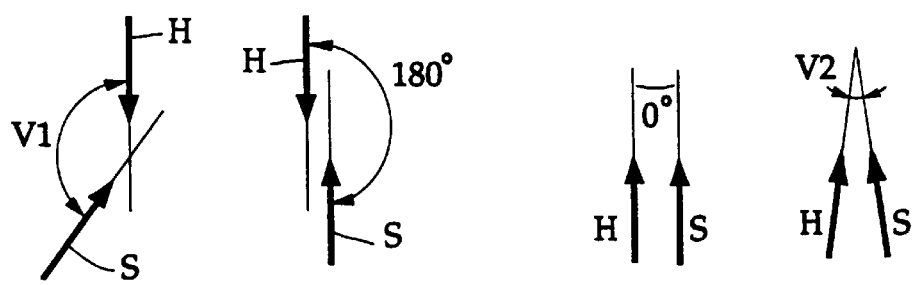
FIG. 13  FIG. 14

NON-INVASIVE OPTICAL MEASURING SENSOR AND MEASURING METHOD

CROSS REFERENCE TO RELATED APPLICATION

The present application is a continuation-in-part application of U.S. patent application, Application Ser. No. 08/757,270, filed Nov. 29, 1996 and now abandoned.

BACKGROUND OF THE INVENTION

The present invention relates to an optical measuring sensor and method for non-invasively measuring the content or composition of one or several chemical components within living tissue, said sensor comprising: a radiation source or radiation sources for emitting measuring radiation with at least two wavelengths to a portion of the body of a patient; detectors or respectively a detector for receiving measuring radiation transmitted through said body portion of a patient and for transforming the same to electrical form; at least one radiation transfer section which is located between either the radiation sources or respectively the detectors and the external surface of said body portion. The invention relates also to the use of such a sensor.

Pulse oximeters are one example for the use of the sensor mentioned above and are capable of measuring the degree of oxygen saturation in a patient's blood non-invasively and continuously. The term non-invasive indicates that the patient is not subjected to subcutaneous penetration by any physical means but the measuring is effected by means of radiation and other than that the procedure occurs externally of the body. This type of monitoring of blood oxygen saturation is quite common today and is one of the monitoring parameters required in many applications. The measurement is optical and based on various absorption characteristics of red and infrared light in blood hemoglobin. The principles of pulse oximetry are disclosed e.g. in Patent publication JP-53-26437. This reference describes a pulse oximeter sensor which comprises a wide-band thermic radiation source and two optical detectors fitted with a bandpass filter for expressing various wavelengths. Other examples for the use of optical sensors mentioned above are a monitor measuring bilirubin concentration in blood as disclosed in publication EP-0 747 002, an instrument analyzing blood glucose as disclosed in publication WO-90/07905, and an apparatus for determining parameters of glucose, protein, albumin, creatinine, carbamide, cholesterol, triglyceride, haemoglobin as disclosed in publication WO-96/37259, etc.

At present, such sensors include two light sources, which are typically light emitting diodes (LED), and a single detector, and the radiation sources are operated alternately in synchronism. In each case, the radiation sources and detectors are included in the sensor itself near a target to be measured and from the sensor extend electrical cables to a control monitor. Usually, the patient experiences no problems when using high-efficiency light sources with a low power consumption. However, the signal-to-noise ratio may sometimes suffer, particularly if for some reason it is desirable to use wavelengths other than those provided by said light sources. In order to achieve as powerful a signal as possible, the light sources can be supplied with a lot of electric power. This may sometimes lead to the situation that, as a result of a higher input of power, the heat generated by light sources affects a target to be measured and causes even burns. Thus, in practice, there is sometimes no choice but to settle for quite a poor signal when sufficient light cannot be produced without coincident heat generation. Neither can the above-described conventional solution be used for example during the course of currently more and more popular magnetic imaging of a patient or while operating some other powerful electromagnetic source. In these conditions, the electrical cable of a sensor would act as an antenna for interferences originating from a control monitor and these interferences would upset the magnetic images. Also other metallic parts at the sensor end disturb a magnetic imager and distort the imaging result. Also in the imaging field, the electric conductor of a sensor may be induced with currents sufficiently strong for a patient to sustain burns or to break down the pulse oximeter equipment. In order to secure more perfect operation in a magnetic imaging environment, the sensor must not include any metallic components at all and, thus, all normal electronics must also be excluded.

Non-invasive optical sensors compatible with the magnetic imaging environment are typically designed with fiberoptics. Hence, the light sources and detector are spaced away from an actual site to be imaged. The light supply is led to and from a site to be measured along optical fibers as described in U.S. Pat. No. 5,103,829. In practice, the fiberoptic cable is a bundle of fibers, comprising a plurality of thin optical fibers and having typically a diameter of 1–3 mm. In order to develop a clinically useful sensor, it is necessary in many cases to bring the bundles of optical fibers to the sensor end in the direction at least roughly parallel to sensor housings. This requires that the light supply be deflected by about 90° inside the sensor housing. The light supply can be deflected by bending the optical fibers to a 90° angle, as disclosed in the publication MEDICAL & BIOLOGICAL ENGINEERING & COMPUTING, Vol. 18/1980 pp. 27–32: Yoshiya, Shimada, Tanaka— "Spectrophotometric monitoring of arterial oxygen saturation in the fingertip." In terms of production, however, this solution is difficult to carry out with sufficiently large bundles of fibers and with a sufficiently small bending radius. The cited glass fibers are easily broken upon bending. Likewise, some of the light supply manages to escape out of the fibers at a sharp curve formed in the fibers.

Other representative fiberoptic designs for a pulse oximeter sensor are described in publications U.S. Pat. No. 5,279,295 and WO-92/21281. In both solutions, the end of a fiber bundle is more or less bent for guiding a light signal to and from a target. In each case, the object of measuring is a patient's finger. In publication U.S. Pat. No. 5,279,295, the monitoring is based on the reflection of light from the finger while publication WO-92/21281 discloses a more conventional solution, wherein the finger is transilluminated. In publication WO-92/21281, the material of a fiberoptic radiation guide is determined to be plastics, i.e. the question is about a plastic fiber, which is probably a little more resistant to bending than glass fiber. However, a drawback in the plastic fiber is that, as pointed out in the publication, its transmittance does not extend very deep into the infrared range, which prevents the use of wavelengths that would be optimal in terms of measuring and also the use of best possible radiation emitting diodes (LED). In these solutions, as well, some radiation may escape out of the sharp fiber curve. The described solutions provide a signal which is poorer than what is achieved if a straight bundle of fibers were orthogonal to the target. Furthermore, the bending of a bundle of fibers is an expensive approach in terms of productivity. Also, the bundle of fibers in the proximity of a target represents a relatively small surface area. A result of this is that the sensor is sensitive to a so-called motion-related artifact. These result either directly from the movements of a target relative to the sensor or from volumetric changes, i.e. absorbency changes, introduced in venous blood by external causes. The harmful effect is further enhanced by the fact that the numerical fiber aperture is relatively small. Normally, a bundle of fibers accepts light rays within the range of ±40° or at best ±60° with respect to the fiber axis. This is modest with respect to a conventional sensor, wherein the source radiates in principle ±90° and also the detector accepts the same amount.

The direction of light supply can also be deflected by means of some external structure, for example a reflective mirror surface. The reflective mirror surface is created e.g. by metallizing a shiny plastic surface for specular reflection or by utilizing a polished prism surface as disclosed in U.S. Pat. No. 5,103,829 for total reflection. However, a metallic or prismatic mirror is not capable of deflecting all radiation supply coming from the fibers. Similarly, a metallic or prismatic mirror is inconvenient in coupling a sufficient amount of tissue-penetrated radiation with a second bundle of fibers and further with the detector. Another downside in a metallic mirror is a metallic layer included therein, which, as a result of evolving eddy currents, may warm up during magnetic imaging and expose the patient to burn hazards. Furthermore, as described above, a metallic layer may disturb magnetic imaging.

SUMMARY OF THE PRESENT INVENTION

A first object of this invention is to provide a non-invasive optical measuring sensor, such as a pulse oximeter sensor, wherein at least one radiation source or at least one bundle of fibers can be used for supplying a target with radiation and/or radiation can be collected from a target to at least one detector or at least one bundle of fibers effectively, advantageously and compactly, which particularly means a high efficiency in the transmission of radiation. A second object of the invention is to provide such a sensor which is not highly sensitive to a motion-related artifact. A third object of the invention is to provide a sensor of this type wherein the heat generated by light sources does not reach a target to be measured but, as a result of the configuration, can be led away therefrom which, if necessary, enables the use of high-power radiation sources. A fourth object of the invention is this type of sensor which does not restrict too severely the use of an otherwise desired infrared wavelength range. A fifth object of the invention is to provide an optical sensor of this type which is suitable for measuring the content or composition of one or several chemical components within living tissue utilizing non-pulsatory or, preferably, pulsatory phenomena in the living tissue.

The above-described drawbacks can be eliminated and the above-defined objects can be achieved by means of a non-invasive optical sensor of the invention, which is characterized by what is set forth in the claims and by the method characterized by what is also set forth in the claims.

In an apparatus of the invention, the light supply can be effectively collected and, if necessary, deflected inside a sensor housing by means of a diffusively reflecting surface. Measuring tests have indicated that, when using this diffusively reflecting surface of the invention in association with optical fibers, the resulting signal is even substantially stronger than that produced by means of target-attached straight or bent fibers. This apparent paradox is explainable by the fact that it is possible to employ larger target areas, as will be manifested herein below. The solution is beneficial since the required materials are inexpensive and it occupies little space since the bundle of fibers need not be bent. In addition, it is possible to employ reasonably priced standard straight fiber bundles instead of expensive and damage-prone special designs. In the proximity of a target to be measured, the light apertures are sufficiently large, such that light can be delivered to the target consistently and also collected therefrom consistently over an area larger than the fiber diameter. By virtue of this, the sensitivity to a motion-related artifact will be insignificant. Conditions permitting, a diffusively reflecting surface of the invention can be used without optical fibers in a sensor equipped with light sources and a detector. Thus, it is preferred that the side facing light sources be provided with a diffusively reflecting surface. This way the light sources are brought further away from a target to be measured and the heat generated thereby is easily carried away from the target.

BRIEF DESCRIPTION OF THE DRAWING

The invention will now be described in detail with reference made to the accompanying drawing figures.

FIG. 10 is a lengthwise cross-section, corresponding to the view of FIGS. 2–9, showing a seventh embodiment for a sensor of the invention, wherein a detector is located remotely from a target to be measured and electric current is brought to and a signal delivered from the sensor along electric conductors and which is designed to be placed on the surface of a patient's body for a measuring technique effected by reflecting from a patient's tissue.

FIG. 11 is a lengthwise cross-section, in a view similar to FIGS. 2 and 3, showing an eighth embodiment for a sensor of the invention, wherein a detector is located remotely from a target to be measured and electric current is brought to and a signal delivered from the sensor along electric conductors and which is designed to be placed on the surface of a patient's body for a measuring technique effected by reflecting from a patient's tissue.

FIG. 12 shows in principle the relative position of those radiation-transmissive end walls whereby the measuring radiation arrives on a diffusively reflective surface of the invention.

FIG. 13 shows in principle the first relative directions of the principal radiating direction for a radiation source assembly of the invention and the principal sensitivity direction for a detector assembly of the invention, corresponding to the embodiments of FIGS. 2–9.

FIG. 14 shows in principle the second relative directions of the principal radiating direction for a radiation source assembly of the invention and the principal sensitivity direction for a detector assembly of the invention, corresponding to the embodiments of FIGS. 10 and 11.

DETAILED DESCRIPTION OF THE PREFERRED EMBODIMENTS

Figure 1:
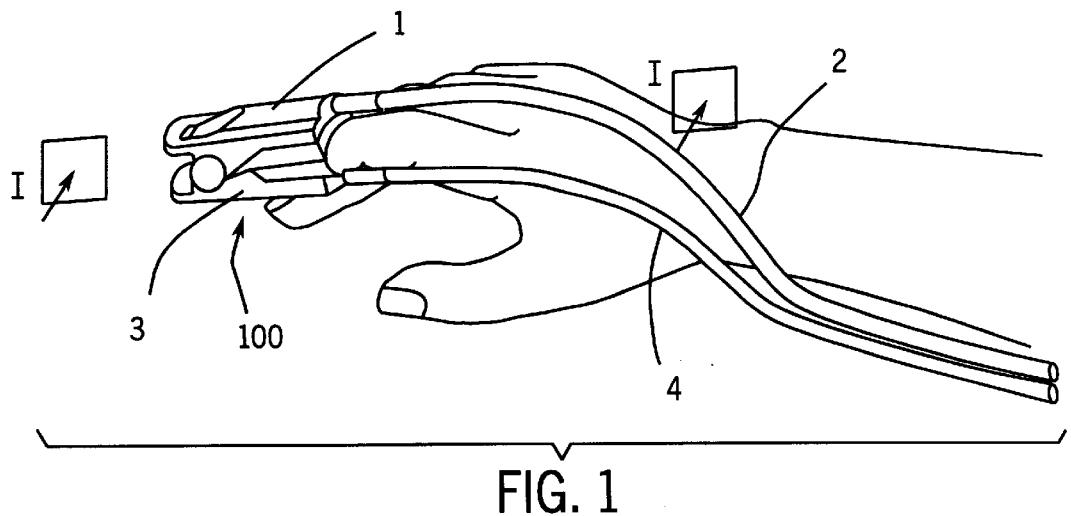
FIG. 1 is a plan view of a typical embodiment for a sensor of the invention, which is fitted with optical fibers for the transfer of radiation and a measuring signal and, thus, for spacing a radiation source and detectors from a sensor itself and which is designed to be fitted on a finger and to operate on a finger-penetrating measuring technique.

The invention will be described using a pulse oximeter an example. A typical pulse oximeter sensor is attached to a fingertip as shown in FIGS. 1 to 3 and 6 to 9. In this application, the expressions radiation and light are used for representing the same thing, i.e. an electromagnetic radiation regardless of a wavelength. In this embodiment, the radiation or light arrives in a top sensor portion 1 along a fiberoptic cable 2 and a light 54 having passed through the finger is collected in a bottom sensor portion 3 for delivering it therefrom along a fiberoptic cable 4 to a detector. In commercially available sensors, the light source generally comprises two diodes (LED) emitting at different wavelengths and the detection of light is generally effected e.g. by means of a single silicon detector, since the applied wavelengths remain within its sensitivity range. Thus, the two radiating diodes (LED) are operated alternately in synchronized manner at an appropriate frequency, whereby signals produced at various wavelengths are distinguishable from each other. There is nothing to exclude the use of even several wavelengths as long as, for example, the present optical fiber is capable of transmitting the same and also other optical components operate in a manner compatible therewith. It is also possible to employ other types of radiation sources, such as thermic emitters or lasers. It is also possible to employ two wide-band radiation sources and two detectors having sensitivities which are adapted, e.g. by means of filters transmissive to narrow wavelength bands, to comply with desired wavelengths. In terms of this invention, neither the wavelength of applied radiation nor the width of a wavelength band nor the number of radiation sources and detectors nor the type of radiation sources and detectors are essential features. In addition to a fingertip, the pulse oximeter sensor can be attached for example to the ear, the palm of a hand, or a toe. In that case, the sensor has a different appearance but the diffusively reflective surfaces of this invention function exactly the same way regardless of a measured target. Therefore, it is primarily a finger sensor that will be studied hereinbelow.

Figure 2:
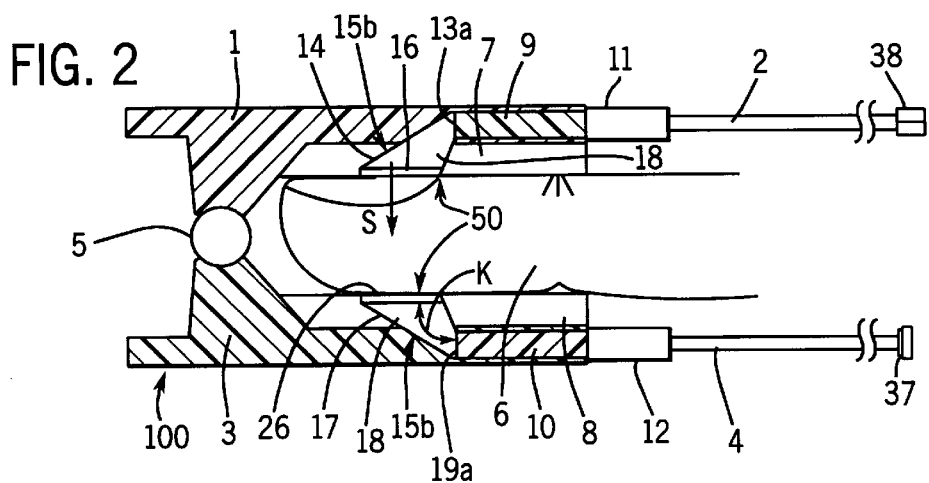
FIG. 2 is a lengthwise cross-section along a plane I–I in FIG. 1, showing a first embodiment for a sensor of the invention, employing fiberoptics for spacing radiation sources and a detector from the actual sensor.

A finger sensor 100 as shown in FIG. 1 is depicted e.g. in FIG. 2 in a lengthwise section. The sensor 100 has its top section 1 and bottom section 3 hinged at 5 in such a manner that both sections of the sensor are capable of opening and closing around a finger 6. Generally, the sensor remains stationary by means of a spring force and a friction developed by pads 7 and 8. Fiberoptic cables 2 and 4, having optical diameters typically in the order of 1–3 mm, are connected to the top and bottom sensor sections 1 and 3 by means of a conventional ferrule 9 and 10 for holding individual fibers in a single bundle and by means of a seal 11 and 12 for providing a durable assembly. The ferrules 9 and 10, like generally all other components in the sensor, are made of materials other than metal if the intention is to employ the sensor in an electromagnetic field. In order to provide a clinically useful sensor, the fiberoptic radiation conductors 2 and 4 arrive in the sensor 100 more or less in the direction of a finger and in general terms the fiberoptic cables arrive in the sensor principally in the direction parallel to the external surface of a target to be measured, in this case an external finger surface 50. Thus, for example in a finger sensor, the optical fibers may arrive in the sensor from the direction of the palm or from the direction of the fingertip or in a direction crosswise to the length of the finger. In a sensor connectable to the earlobe, the optical fibers arrive typically in the direction of the earlobe, and in a sensor to be fitted inside the ear, in the direction of the external auditory canal. The use of fiberoptic radiation conductors enables all metallic and electric components to be placed remotely from the actual sensor 100, such as in connection with the actual measuring monitor or in some converter between sensor and monitor. The distance is selected to be sufficient for any given application, such that the pulse oximeter sensor does not cause trouble or be troubled itself. When using a diffusively reflective surface of the invention, the optical radiation conducting fiber may comprise a glass fiber which is well transmissive even to quite long-wave infrared radiation since, in a solution of the invention, the fiber need not be bent for bringing the radiation to a desired angle, i.e. generally to an orthogonal direction, relative to the external surface 50 of the target 6.

The light, arriving from a radiation source 38 along a fiber cable 2, exits from the fiber end at a point provided with an inner end wall 13a included in a radiation transfer section of the invention, as a beam of scattering light having an opening angle around the center axis typically of ±40° and with wide-angle fibers ±60°. A small portion of this light may fall on the external surface 50 of the finger 6 but most of it falls on a diffusively reflective surface 14 of the invention, which is included in a cavity 18 and has a funnel-like shape as shown in the figure and opens towards the target 6. Preferably, the inner end wall 13a of the cavity 18 has a surface area which is in the same order as the cross-sectional area of the bundle of fibers and the surface area of an outer end wall 16 in the direction of at least roughly parallel to the finger surface 50 is larger than that. Thus, the cavity 18 diverges towards a target. The radiation arrives at the transfer section by way of the inner end wall, progresses by way of the diffusively reflective surface 14 and penetrates into a target to be measured through the outer end wall. Thus, depending on the fiber 2, the inner end wall 13a may have a diameter of e.g. 1–3 mm and a preferred diameter for the outer end wall 16 is for example about 7 mm, which enables the scattering of light over a larger surface area and the sensitivity to a motion-related artifact remains insignificant with no light escaping from source to detector without passing through a target. Also, a large surface area complies better with the pulse oximeter's calibrating curve used for determining the relationship with the oxygen content of blood as the local inhomogeneities of a target, such as bone-induced shadings or individual venous blood vessels, are not able to have as strong an effect on the measuring result as would be the case with a smaller outer-end-wall surface area. In terms of operation, the surface areas of the apertures may have any given ratio but, in practice, it is thus preferred that the aperture which opens towards a target to be measured be larger. In a typical case, the outer end wall has a surface area which is at least double with respect to that of the inner end wall but it can be even considerably larger, e.g. tenfold.

Figure 5A:
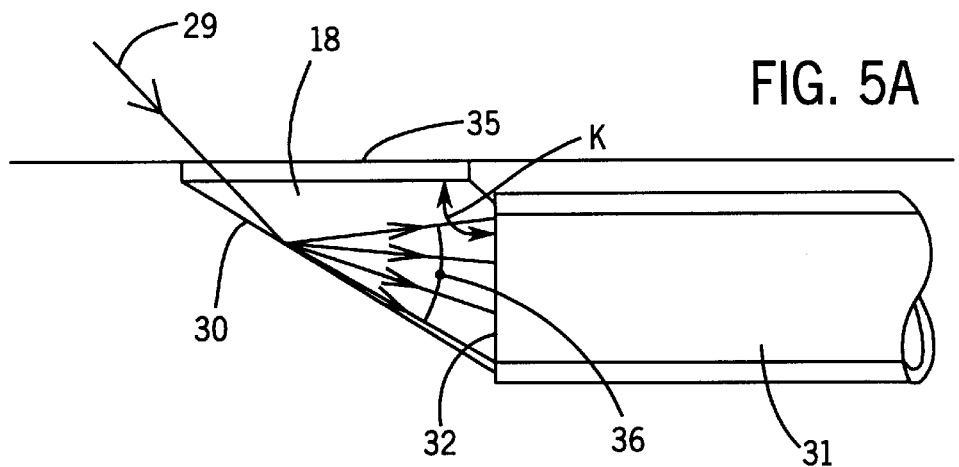
FIGS. 5A and 5B depict the behavior of a diffusively reflective surface of the invention with radiation arriving thereon from various angles of incidence.
Figure 5B:
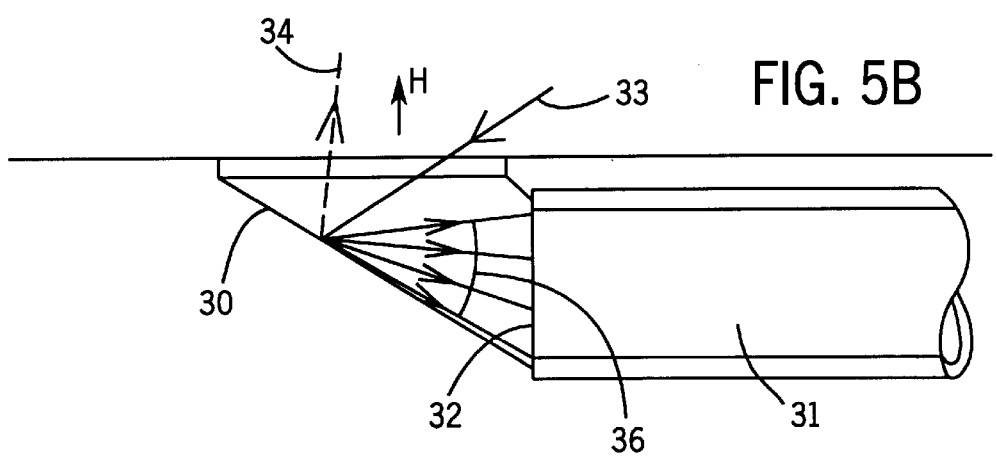

The exact configuration of the diffusively reflective surface 14 is not critical, either. It can be a slanting cone 15b, as in FIG. 2, but some other configuration, such as an arched-surface funnel 15c shown in FIG. 3, functions equally well. In the embodiment of FIGS. 5A–5B, the funnel can be an oblique wedge, whereby a diffusively reflective surface 30 is flat or a slanting cone or cylinder, said diffusively reflective surface 30 being concave towards the inside of a cavity 18. In the former case, the image-plane facing cross-section of the cavity is a rectangle and in the latter case it is a circle or an ellipse. If it is flat, the diffusively reflective surface should be preferably arranged at least in a roughly orthogonal attitude towards the bisector of an angle formed by the inner-end-wall normal and the outer-end-wall normal together, as shown e.g. in FIGS. 5A–5B. As for the arched funnel 15c, on the other hand, it is appropriate to arrange the inner end wall and the outer end wall in such a manner that the normals thereof intersect the diffusively reflective surface or a surface section or an extension thereof, in other words the normals of the end walls must be directed towards the diffusively reflective surface. The aperture of the outer end wall 16 of a funnel is preferably covered e.g. with a window for preventing dirt from finding its way into the cavity 18 and further onto the end surface of a bundle of fibers or onto the diffusively reflective surface. The window may be constructed e.g. of silicone or some other appropriate material. Another option is to fill the entire cavity 18 with a light transmitting material, for example with similar transparent silicone. This is not harmful for the proper function of a diffusively reflective surface. It is obvious that the inner and outer end wall can be sealed with windows made of an appropriate material and the cavity 18, 41 filled with an appropriate gas or liquid.

Having passed through the finger, the light is completely scattered and, at the point of measuring, each spot of the finger operates as a Lambertian source. Light is arriving from quite a wide range and the effective collection thereof on the end-wall surface of the fiber or bundle of fibers 4 is not easy no matter which of the actually occurring diameter and opening angle is used for the fiber or bundle of fibers. Nevertheless, the fiber 4 should be capable of carrying to a detector 37 as much as possible of the radiation coming from a target to be measured. A diffusively reflective surface 17 similar to the surface 14 contributes even on the radiation collection side to an increased collecting efficiency, as pointed out hereinafter. In terms of its dimensions, it can be similar to the funnel surface 14 but it may also have some other configuration, particularly if the fiber bundles 2 and 4 are different from each other. Thus, the collection of radiation from a target 6 is effected by means of a similar type of cavity 18 as the supply of radiation to the target 6, said cavity 18 thus including an inner end wall 19a, by way of which the collected radiation transfers to the fiber 4, as well as an outer end wall 26, by way of which the radiation enters inside the cavity to be subsequently reflected from the diffusively reflective surface 17. The design can be totally analogous to the above-described radiation supplying cavity. Thus, the outer end wall 26 has a surface area which preferably exceeds that of the inner end wall 19a, typically the outer end wall has surface area which is at least double with respect to that of the inner end wall, but it may be even considerably larger, e.g. tenfold. In view of the actual operation, the apertures may have surface areas whose ratio to each other can be anything, as already described above. Also in this case, the end walls must have the normals thereof directed towards the diffusively reflective surface or an extension thereof, as explained above. Even in this case, the aperture in the outer end wall 26 of the funnel can be covered with transparent silicone or some other compatible material or the entire cavity 18 filled with this material without disturbing operation of the diffusively reflective surface.

Figure 3:
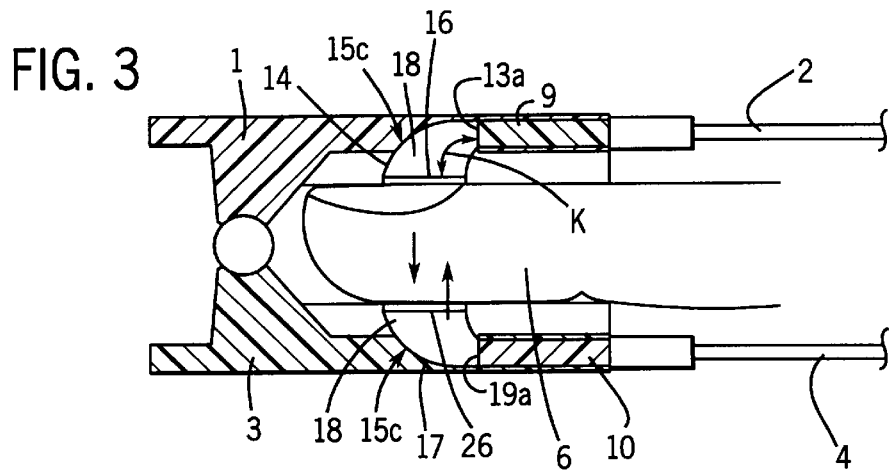
FIG. 3 is a lengthwise cross-section along a plane I–I in FIG. 1, showing a second embodiment for a sensor of the invention, employing fiberoptics for spacing radiation sources and a detector from the actual sensor.
Figure 6:
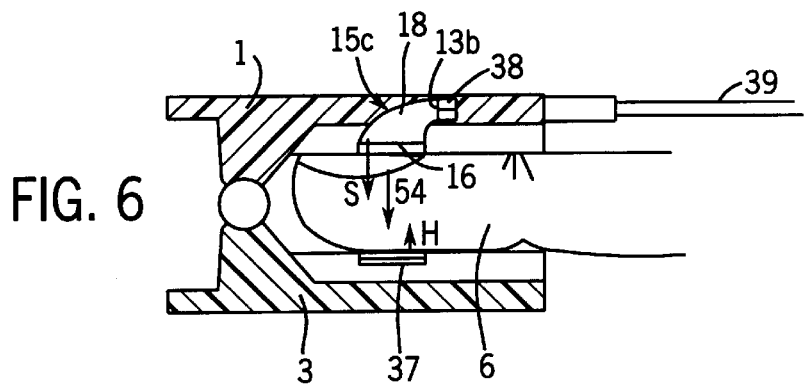
FIG. 6 is a lengthwise cross-section, in a view similar to FIGS. 2 and 3, showing a third embodiment for a sensor of the invention, wherein light sources are located remotely from a target to be measured and electric current is brought to and a signal delivered from the sensor along electric conductors.
Figure 7:
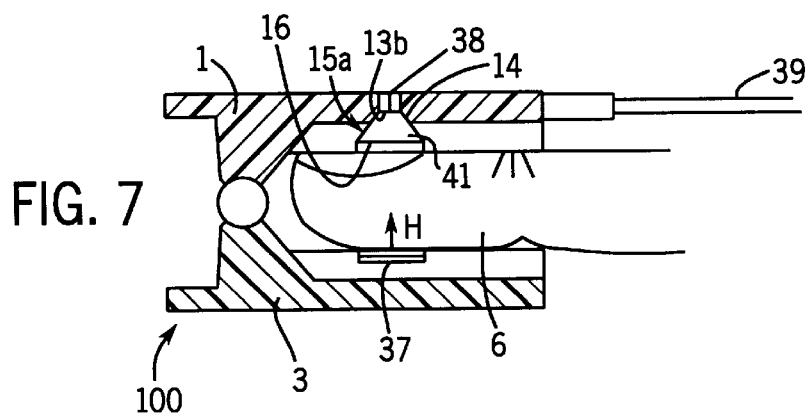
FIG. 7 is a lengthwise cross-section, in a view similar to FIGS. 2 and 3, showing a fourth embodiment for a sensor of the invention, wherein light sources are located remotely from a target to be measured and electric current is brought to and a signal delivered from the sensor along electric conductors.
Figure 8:
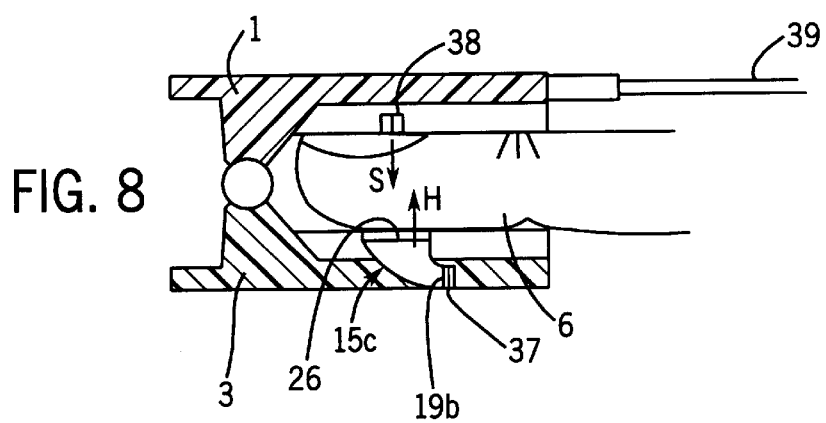
FIG. 8 is a lengthwise cross-section, in a view similar to FIGS. 2 and 3, showing a fifth embodiment for a sensor of the invention, wherein a detector is located remotely from a target to be measured and electric current is brought to and a signal delivered from the sensor along electric conductors.
Figure 9:
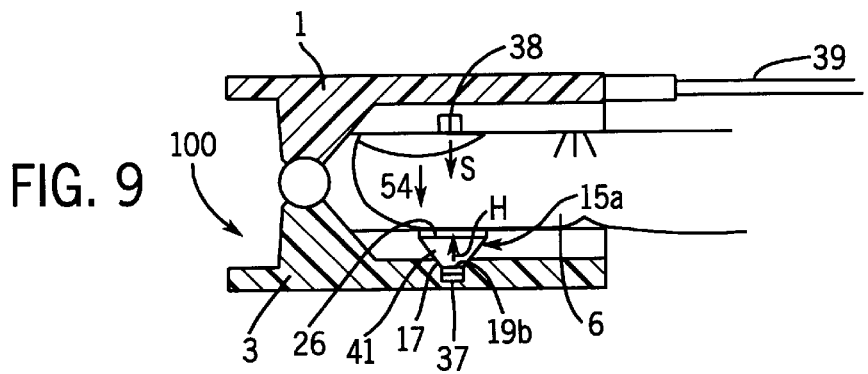
FIG. 9 is a lengthwise cross-section, in a view similar to FIGS. 2 and 3, showing a sixth embodiment for a sensor of the invention, wherein a detector is located remotely from a target to be measured and electric current is brought to and a signal delivered from the sensor along electric conductors.

In the above-described embodiments of FIGS. 2 and 3, in the embodiment of FIGS. 5A and 5B, as well as partially in the embodiments of FIGS. 6 and 8, the cavity 18 is provided with inner end walls 13a, 19a, 13b, 19b and 32 which form an angle K relative to the outer end wall 16, 26 and 35 of the cavity, said angle being within the range of 30°–100°, generally at least 45°, preferably within the range of 60°–95° and typically about 90°. This angle is explained further in FIG. 12. In FIGS. 2–3, 5A–5B, 6 and 8, the angle K is essentially a right angle, but if so required by a particular application, it can be somewhat more than 90°, as pointed out above. This described angle configuration enables the passage of the fiberoptic radiation conductor 2, 4 to a sensor e.g. in the direction of the external surface 50 of a target or in some other appropriate direction without having to bend the optical fiber. Naturally, the inner end walls 13b and 19b can be perfectly or approximately parallel to the given respective outer end wall 16 and 26, as depicted in FIGS. 7 and 9 and to be subsequently described in more detail. In any event, between the inner end wall and the outer end wall is fitted a diffusively reflective surface of the invention. The outer end wall is set against the external surface of a target to be measured, whereby a slight gap is often left therebetween no matter if the question is about the side supplying radiation to a target or the side collecting radiation from a target. The inner end wall refers to a point of contact with an optical fiber or some other radiation conducting element or with radiation sources or a detector or a like. In theory, it is not absolutely necessary that a jacket of the cavity 18 be provided between the end walls to surround the end walls as well as the diffusively reflective surface although, in practice, the cavity and its jacket are normally necessary for avoiding external mechanical and physical and chemical drawbacks.

Figure 4:
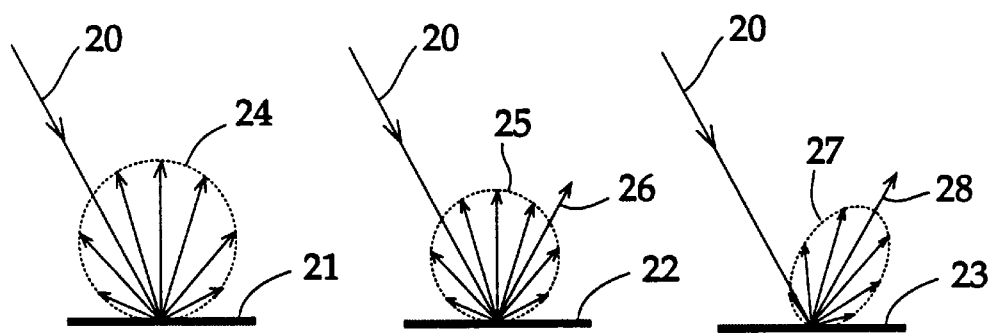
FIG. 4 shows graphically the reflection characteristics of diffusively reflective surfaces of the invention.

The qualities of a diffusively reflective surface are depicted in FIG. 4. A ray of light 20 falls on various types of diffusively reflective surfaces 21, 22 and 23. The roughness of a surface and the optical characteristics of a material determine how the ray is reflected. It is of course desirable that the surface does not absorb the applied radiation and that the material is not so thin that the light is able to escape therethrough. The light may reflect directly from the surface or it may travel deeper in a diffusively reflective material prior to reflecting back. The surface 21 is a so-called Lambertian surface which completely scatters the light 20 fallen thereon. In that case, the roughness of a surface material or the size of the structural elements of a material is lesser than or in the same order as the light's wavelength. The light scatters in every direction such that the reflected radiation has an intensity distribution which follows a dotted line 24 (the distribution is represented by a sphere which is tangential with the reflective surface, the intensity vectors starting from tangential points and terminating at the ball surface). Such a surface appears equally bright from every direction and is theoretically the best possible scattering surface, i.e. a diffusively reflective surface. Such a surface is difficult to manufacture, but for example Labsphere, Inc. is marketing a material called Spectralon, having characteristics which are very close to those of the surface 21. The same type of material is also available as a coating. The materials and coatings have a reflectance of about 99%, hence the absorption and transmission are insignificant. The surface 22 depicts a case in which a scattering section 25 is significant but in which also a mirror reflection 26 of the surface is visible. It is useful also in a sensor of the invention although the efficiency is slightly poorer than what is achieved by the surface 21. Several scattering materials belong in this category. For example, the commercially available silicone polymers, which are readily mouldable to a proper shape, may remain slightly shining over the surface thereof, and, thus, some mirror reflection is inevitable. However, the mirror reflection of a surface has an intensity whose proportion is generally modest with respect to the diffusively reflected intensity, since the mirror reflection depends on the index of refraction of a material, which on silicone polymers is relatively low, and since the material is non-metallic. The surface 23 is rougher than the surfaces 21 and 22, as evidenced by the fact that an intensity distribution 27 is an ellipse or ellipsoid parallel to a mirror reflection 28. However, the scattering or ray-diffusing effect continues to be dominant. The ray-diffusing results from the fact that light reflects from various roughness patterns of a surface in directions other than the one in which the radiation would reflect from a common mirror surface and, hence, the intensity patterns resembles a scattering pattern. Generally, the practical diffusively reflective surface is a combination of all surfaces shown in FIG. 4. Although non-metallic materials are in most cases used in diffusively reflective surfaces it is not inconceivable, in principle, to employ a suitably surface-treated metal as well, if the particular application allows the use of metal in the sensor. A metal treated to be diffusively reflective may be the only solution when it is necessary to use extremely long wavelengths. However, this is not the case in a normal pulse oximeter sensor and, thus, the use of non-metallic materials is plausible.

FIGS. 5A and 5B illustrate how the diffusively reflective surface operates as a light collecting system and why its use is preferred. In FIG. 5A, a ray 29 arrives from a radial direction preferable in terms of mirror reflection from a diffusively reflective surface 30, which can be any of the surfaces 21, 22 or 23 depicted in FIG. 4. Even after the mirror reflection, the ray would be likely to fall on the end-wall surface of a bundle of fibers 31, which is in alignment with an inner end wall 32, since the bundle of optical fibers 31 accepts all angles 36 smaller than the flare angle of the fiber. In FIG. 5B, on the other hand, a ray 33 arrives from such a direction that the mirror reflection would take it completely out of the system as a ray 34. This is not preferred, although it is possible to presume that a portion of the ray, having reflected again from the surface of a target, arrives in the funnel, be it in a decisively weakened condition. Presuming subsequently that the surface 30 is totally diffusively reflective, i.e. a so-called Lambertian surface mentioned above, and performing a comparison between such a diffusively reflective surface of the invention and a bundle of fibers in direct contact with a target. Supposing further that the bundle of fibers 31 has a diameter of 2 mm in keeping with the diameter of the inner end wall 32 and that an outer end wall 35, i.e. an inlet aperture, included in the cavity 18 and opening towards the target, has a diameter of 7 mm. The operating principle of a diffusively reflective cavity is the same as that of an integrating sphere and, thus, it is possible at a sufficient accuracy to apply computation formulae relating to an integrating sphere. The cavity includes two apertures 32 and 35, as generally found in an integrating sphere. As an exception from the normal integrating sphere it is possible to accept the fact that some radiation advances directly from aperture 35 to aperture 32 without hitting the cavity wall, in other words, the aperture 35 is visible from the aperture 32. This is beneficial in terms of the invention as there will be no reflection losses. It is contemplated, however, that the entire radiation falls at least once on the diffusively reflective surface 30. A portion T2 of the intensity arriving in the aperture 35, which exits from aperture 32, will thus be $$T2=f2*R_w/[1-R_w*(1-f1-f2)-R1*f1],$$

wherein f1 and f2 represent the ratio of the surface areas of aperture 32 and 35 to a surface area A of the entire cavity, $R_w$ is a reflection factor for the diffusively reflective surface and R1 is a reflection factor for the outer end wall 35 or, more precisely, for the external surface 50 of the target 6. The value of the surface area A is not highly critical although a small value seems to be beneficial in this case. The value given in this example is 100 mm². The reflection factor for the cavity was measured with the use of white silicone as $R_w=0.93$ and the reflection factor for a target, i.e. the human skin, was estimated, as measured with red light, to be R1=0.6. Thus, the reflectivity of the target 6 is generally also contributing to the signal. Using these values, the resulting transmission will be T2=0.13. A surface of the target 6 defined by the aperture 35 contains diffusively transmitting Lambertian sources $(7/2)^2=12.25$ times more than what could be directly accommodated by the aperture 32, i.e. a higher number of sources in terms of the ratios between surface areas of the apertures. Thus, the gain of collection would be 0.13*12.25=1.59 i.e. the result will be a signal more than one and a half times stronger than what could be produced by collecting directly with the fiber end. The performed measurements have clearly supported this theory, although the augmentation of a signal has been slightly lesser than calculated, probably due to an imperfect contact between target 6 and the outer end wall of cavity 18, a lower-than-expected reflection factor for the target, and inhomogeneous lighting of the target.

Thus, with a larger surface are of the outer end wall 16, 26 and 35 it is possible to collect more light on the inner end wall 13a, 13b, 13c, 19a, 19b and 32 by using the diffusively reflective surface 14, 17, 21–23, 30 between the target 6 and a radiation source or a detector, e.g. in the cavity 18, 41, and at the same time the direction of radiation coming from the target can be deflected as desired or, in this case, to comply with the direction of the optical fiber 4, 31. Other benefits from using a larger surface area include a reduced sensitivity to a motion-related artifact, be it a directly external disturbance or an internal disturbance resulting for example from volumetric changes in venous blood.

The foregoing has described but a few examples of how a diffusively reflective surface or material can be utilized in a pulse oximeter sensor operating on fiberoptics. It is obvious that there are other conceivable types of solutions based on the same principle of diffusive reflection. The optical fiber is not absolutely necessary for proper functioning of the inventive principle, although a fiberoptic pulse oximeter sensor is a preferred application. Even a conventional sensor, wherein light sources 38 and a detector 37 are included in a sensor 100 closer to a target 6 to be measured, can be improved by using diffusively reflective surfaces in accordance with the invention. One such solution is depicted in FIG. 6. In this solution, a detector 37 is located close to a target 6 to be measured, as in traditional sensor designs. On the other hand, the light sources 38, normally two diodes (LED) emitting at different wavelengths, are, according to the invention, mounted on an inner end wall 13b included in a diffusively reflective cavity 15c. In principle, the number of radiation sources 38 can be more than two, if so required by a particular application, or a more-than-normal amount of power can be supplied thereto. A higher light supply improves the signal-to-noise ration, which otherwise may be too poor in certain operating conditions. The increased power consumption and the accompanying rise in temperature are not, in this assembly, focused on a target 6 to be measured but can be effectively guided to a top unit 1. This serves to eliminate possible heat-inflicted damages in the target 6 to be measured. In addition, the effect on a measuring result due to the position of various light sources will be equalized. Electric supply signals from both the detector 37 and the light sources 38 are carried along an electric cable 39 to a control monitor.

FIG. 7 illustrates another corresponding solution, wherein a diffusively reflective surface 14 included in a cavity 41 is not laterally curving but, instead, a direct cone 15a facing straight towards a target 6 and having its inner end wall 13b, along with radiation sources 38 included therein, at such a distance from the target 6 to be measured that eventual generated heat can be delivered away from the target to a frame 1. The cavity-forming direct cone 15a has a function otherwise similar to slanting or arching funnels 15b and 15c except that the proportion of direct light from sources to target is higher. If the funnels 15a–c reflect diffusively at a high efficiency, the signal should indicate no difference between the different types of cavities 18 and 41.

The detector may also utilize a diffusively reflective cavity for example for eliminating the effect of a motion-related artifact, as in the solution shown in FIG. 8. In this solution, light sources 38 are located close to the surface of a target 6 but could just as well be located further away from a target according to FIG. 6 or 7. A detector 37 is further away from the surface of the target 6 at an inner end 19b included in a cavity, which is provided with a diffusively reflective surface and is, in this case, an arched funnel 15c. Exactly the same way as in the solution of FIG. 7, the detector 37 may also be directed straight towards the target 6, as shown in FIG. 9, by using an appropriately shaped direct cone 15a as a cavity 41. In the solutions shown in FIGS. 8 and 9, the detector 37 can be used for indicating light from a larger surface section of the target 6 and, as pointed out above, for producing even more signal than could be achieved if the detector were in a conventional manner close to the target surface.

All the above pulse oximeter sensors have been ones that are based on a transmission measured straight through a target. Thus, a direction S of the principal radiation from a radiation source 38 and/or a respective diffusively reflective surface and a principal sensitivity direction H indicated by way of a detector and/or a respective diffusively reflective surface are substantially opposite to each other, i.e. form a relative angle of 180° or form an obtuse angle V1, as illustrated in FIG. 13. This produces a light 54 passing directly through a target for obtaining a measuring signal.

There is nothing to stop applying the inventive principle also to a pulse oximeter sensor 101 operating on a reflection principle. In this type of preferred sensor configuration, as shown e.g. in FIG. 10, it is important that light sources 38 and a detector 37 be located side by side in the direction of an external target surface 50 at such a distance from each other that a light 44 is forced to progress through an arterial-blood containing tissue of a target 6 to be measured prior to reflecting back instead of traveling along the surface layer of a tissue. A cavity 41, including a diffusively reflective surface and having its inner end wall 13c provided with a detector 37, is also in this type of sensor capable of collecting more light from deep in the tissue than what could be achieved if the detector were in a direct contact with the target 6. The sensor assembly is generally provided with just one body element 42 and a pad 43, sometimes combined, on which light sources and a detector are mounted and from which a signal is delivered for further processing by way of a cable 39. The sensor 101 can be fastened to a target by means of a tape, a rubber band or by other respective means. Although the described sensor is electric, there is nothing that would prevent the use of optical fibers for this solution as well, as already explained above. The cavity 41, shown in FIG. 10 and including a diffusively reflective surface, only measures light over one side of the light sources. The aperture in the cavity 41, opening towards a target 6, need not be circular as some other appropriate shape is equally suitable. FIG. 11 depicts a configuration for radiation sources 38 effectively collecting radiation reflected from the entire environment. In this solution, the light sources 38 are located in the middle of an outer end 26 included in the cavity 41 provided with a diffusively reflective surface and at least close to the plane of said outer end, in other words, the light sources and detectors are fitted within each other. Thus, the detector 37, which is located in alignment with an inner end 13c of the cavity, receives reflected light 44 from as large as possible a target surface area. The light sources 38 are optically insulated from the cavity 41 with a light blocking surface 45, which surrounds the light sources in the direction of the outer end, whereby the light being collected in the cavity has inevitably been forced to travel deep in the tissue. In this case, the cavity 41 is preferably filled with a transparent material, such as silicone. In the embodiments of FIGS. 10 and 11, a direction S of the principal radiation from a radiation source 38 and/or a respective diffusively reflective surface and a principal sensitivity direction H indicated by way of a detector and/or a respective diffusively reflective surface are substantially co-directional, i.e. form a relative angle of 0° or form an acute angle V2, as illustrated in FIG. 14. This produces a light 44 reflecting from the tissue of a target for obtaining a measuring signal.

The disclosed embodiments are but examples of how a diffusively reflective cavity can be used in a non-invasive measuring sensor. It is self-evident that other representative solutions exist as well. For example, it is conceivable to use just a single light source and respectively two or more detectors, although the above-described configurations are most common.

Thus, it is not a requirement in this invention that both the radiation sources 38 and the detectors 37 be provided with diffusively reflective surfaces but either one is nevertheless equipped with a diffusively reflective surface fitted between the external target surface 50 and a radiation source or a detector. Conditions permitting, the sensor may only be provided with one above-mentioned funnel, either on the inlet or outlet side, which provides a diffusively reflective surface. A second funnel is then replaced by another type of construction, such as electronic components or a different fiberoptic system. In principle, the funnel may be nearly any shape at all. FIG. 2 illustrates a slanting cone 15b, FIGS. 3, 6 and 8 depict an arched cone 15c, and FIGS. 7–8 and 10–11 show a direct cone 15a. The slanting wedge illustrated in conjunction with FIGS. 5A–5B is a special case among these funnels. The funnel, which forms a cavity 18, 41, need not be diffusively reflective over its entire inner surface, although it is most preferred. If necessary, it is possible to employ such a diffusively reflective surface, towards which the sensitive surface of detectors and/or respectively the emitting surface of radiation sources and/or the end of an optical fiber are directed. The rest of the interior of an eventual cavity 18, 41 can be made of another type of material, e.g. some more or less radiation-absorbing material. For example, if in the case of FIGS. 5A–5B, the diffusively reflective surface 30 is flat and orthogonal to the image plane, the ends not shown in the figures and extending parallel to the image plane can be non-diffusively reflective. However, it is preferred that as large a portion as possible of a radiation transfer section fitted between the inner end and the outer end be designed as diffusively reflective according to the invention.

As noted above, the sensor of the present invention can be used for measuring the content or composition of one or several chemical components within a tissue of a body portion, using different wavelengths or wavelength bands of radiation of a non-pulsatile or, preferably, a pulsatile nature. The body portion may be an ear, a palm of a hand, a toe, or any other suitable body portion. The different wavelengths are selected to be proper for use with the chemical component being measured, as is a general praxis in the technological field of radiation absorption analysis. Thus, the wavelengths can be selected for detecting, e.g. the oxygen saturation in a patient's blood or for detecting the composition or content of such chemicals, as bilirubin, glucose, protein, albumin creatinine, carbamide, cholesterol, triglyceride, haemoglobin, alcohol, carbon dioxide, oxygen, oxygen saturation, anaesthetics, particularly those dosed in the liquid state, urea, hematocrit, etc., or for detecting any of the composition or content of a further chemical as needed or possible.

It is recognized that modifications may be made to the sensor and method disclosed above and it is intended to include all such modifications and equivalents as fall within the scope of the following claims.

We claim:

1. A non-invasive optical sensor for measuring the content or composition of one or more chemical components within a tissue of a body portion, said sensor being suitable for being placed on a selected portion of the patient's body, said sensor comprising:

a radiation source for emitting radiation having at least two wavelengths, the radiation being applied to an external surface of the body portion for transmission into the body portion when the sensor is placed on the body portion;

a detector for receiving radiation from an external surface of the body portion and for providing a signal evincing a property of the received radiation when the sensor is placed on the body portion; and at least one radiation transfer section, said radiation transfer section having a first end aperture facing an external surface of the body portion when the sensor is placed on the body portion, said radiation transfer section having a second end aperture coupled to one of said radiation source and detector, the area of said first end aperture being greater than the area of said second end aperture, said radiation transfer section having a diffusely reflective surface for receiving radiation entering said radiation transfer section from one of said end apertures and transferring same to the other of said end apertures, said diffusely reflective surface comprising a surface formed to have diffusely reflective properties approaching those of a Lambertian surface so that generally uniform scattering of the received radiation by the diffusely reflective surface predominates.

2. A non-invasive optical sensor for measuring the content or composition of one or more chemical components within a living tissue of a body portion, said sensor utilizing a pulsatory phenomenon of said body portion and being suitable for being placed on a selected portion of the patient's body, said sensor comprising:

a radiation source for emitting radiation having at least two wavelengths, the radiation being applied to an external surface of the body portion for transmission into the body portion when the sensor is placed on the body portion;

a detector for receiving radiation from an external surface of the body portion and for providing a signal evincing a property of the received radiation when the sensor is placed on the body portion; and at least one radiation transfer section, said radiation transfer section having a first end aperture facing an external surface of the body portion when the sensor is placed on the body portion, said radiation transfer section having a second end aperture coupled to one of said radiation source and detector, the area of said first end aperture being greater than the area of said second end aperture, said radiation transfer section having a diffusely reflective surface for receiving radiation entering said radiation transfer section from one of said end apertures and transferring same to the other of said end apertures, said diffusely reflective surface comprising a surface formed to have diffusely reflective properties approaching those of a Lambertian surface so that generally uniform scattering of the received radiation by the diffusely reflective surface predominates.

3. A pulse oximeter sensor for non-invasively measuring the degree of oxygen saturation in a patient's blood, said sensor being suitable for being placed on a selected portion of the patient's body, said sensor comprising:

a radiation source for emitting radiation having at least two wavelengths, the radiation being applied to an external surface of the body portion for transmission into the body portion when the sensor is placed on the body portion;

a detector for receiving radiation from an external surface of the body portion and for providing a signal evincing a property of the received radiation when the sensor is placed on the body portion; and at least one radiation transfer section, said radiation transfer section having a first end aperture facing an external surface of the body portion when the sensor is placed on the body portion, said radiation transfer section having a second end aperture coupled to one of said radiation source and detector, the area of said first end aperture being greater than the area of said second end aperture, said radiation transfer section having a diffusely reflective surface for receiving radiation entering said radiation transfer section from one of said end apertures and transferring same to the other of said end apertures, said diffusely reflective surface comprising a surface formed to have diffusely reflective properties approaching those of a Lambertian surface so that generally uniform scattering of the received radiation by the diffusely reflective surface predominates.

4. The sensor of claim 1, 2 or 3 wherein said radiation transfer section has a cavity between said first and second end apertures and wherein said diffusively reflective surface is in said cavity.

5. The sensor of claim 4 wherein said cavity is generally funnel shaped.

6. The sensor of claim 5 wherein said funnel shaped cavity is formed about a generally central line that extends between said first and second end apertures, and wherein said funnel shaped cavity is formed such that said central line is normal to one of said first and second end apertures.

7. The sensor of claim 5 wherein said funnel shaped cavity is formed about a generally central line that extends between said first and second end apertures, and wherein said funnel shaped cavity is formed such that said central line slants with respect to one of said first and second end apertures.

8. The sensor of claim 5 wherein said funnel shaped cavity is formed about a generally central line that extends between said first and second end apertures, and wherein said funnel shaped cavity is formed such that said central line is curved between said first and second end apertures.

9. The sensor of claim 4 wherein said cavity has a window member across said first end aperture.

10. The sensor of claim 4 wherein said cavity is filled with a light transmitting substance.

11. The sensor of claim 10 wherein said cavity is filled with a silicone compound.

12. The sensor of claim 10 wherein said cavity is filled with gas.

13. The sensor of claim 4 wherein said cavity is formed in a body of said sensor.

14. The sensor of claim 1, 2 or 3 wherein the area of said first end aperture is at least twice the size of the area of said second end aperture.

15. The sensor of claim 1, 2 or 3 wherein said first and second end apertures lie in planes, and wherein said end apertures are positioned in said radiation transfer section so that the planes subtend an angle in a range of 30°–100°.

16. The sensor of claim 15 wherein said angle is at least 45°.

17. The sensor of claim 16 wherein said angle is in a range of 60°–95°.

18. The sensor of claim 15 wherein said angle is 90°.

19. The sensor of claim 1, 2 or 3 wherein said first and second end apertures are positioned in said radiation transfer section to lie generally parallel to each other.

20. The sensor of claim 1, 2 or 3 wherein said diffusively reflective surface is flat.

21. The sensor of claim 1, 2 or 3 wherein said diffusively reflective surface is curved.

22. The sensor of claim 1, 2 or 3 wherein said diffusively reflective surface is formed such that an intersection of said surface and a plane normal to said end apertures presents a straight line, wherein said first and second end apertures lie in planes positioned at an angle to each other so that normals to said end apertures intersect, and wherein at least a portion of said reflective surface is generally normal to a bisector of the angle subtended by said intersecting normals.

23. The sensor of claim 1, 2 or 3 wherein said diffusively reflective surface is formed such that the intersection of said surface and a plane normal to said end apertures presents a curved line and wherein said end apertures lie in planes positioned at an angle to each other such that normals to said end apertures intersect said diffusively reflective surface.

24. The sensor of claim 1, 2, or 3 wherein said diffusively reflective surface is formed of a material having surface roughness and optical characteristics providing said diffusively reflective properties.

25. The sensor of claim 1, 2 or 3 wherein said diffusively reflective surface has a coating providing said diffusively reflective properties.

26. The sensor of claim 1, 2 or 3 wherein said sensor includes two of said radiation transfer sections, and wherein said radiation source is coupled to said second end aperture of one of said sections and said detector is coupled to said second end aperture of the other of said sections.

27. The sensor of claim 26 wherein both said radiation source and said detector are coupled to a second end aperture of a radiation transfer section by an optical fiber member.

28. The sensor of claim 26 wherein both said radiation source and said detector are positioned immediately proximate to a second end aperture of a radiation transfer section.

29. The sensor of claim 1, 2 or 3 wherein at least one of said radiation source and said detector is coupled to said second end aperture of said radiation transfer section by an optical fiber member.

30. The sensor of claim 27 wherein one of said radiation source and detector is coupled to a second end aperture of a radiation transfer section by an optical fiber member and wherein the other of said radiation source and detector is positioned immediately proximate to a second end aperture of a radiation transfer section.

31. The sensor of claim 1, 2 or 3 wherein said radiation source is coupled to said second end aperture of said radiation transfer section by an optical fiber member and wherein the size of said second end aperture approximates a cross sectional area of said optical fiber means.

32. The sensor of claim 1, 2 or 3 wherein at least one of said radiation source and said detector is positioned immediately proximate to a second end aperture of said radiation transfer section.

33. The sensor of claim 1, 2 or 3 wherein said radiation source is located in said first end aperture of said radiation transfer section and said detector is coupled to said second end aperture of said radiation transfer section.

34. The sensor of claim 1, 2 or 3 wherein said sensor is defined as one for placing said radiation source on one surface of the selected portion of the patient's body and placing said detector on a second surface of the selected portion of the patient's body lying generally opposite said first surface.

35. The sensor of claim 1, 2 or 3 wherein said sensor is defined as one for placing said radiation source and said detector in adjacent positions on a surface of a selected portion of the patient's body.

36. A method for non-invasively measuring the content or composition of one or more chemical components within a tissue or body portion, said method comprising the steps of:

emitting radiation having at least two wavelengths suitable for carrying out the measurement;

applying the radiation to a surface of a selected portion of the patient's body;

detecting radiation from a surface of the selected portion of the patient's body, the radiation evincing a property of the received radiation indicative of the chemical component;

providing a signal indicative of the chemical component content or composition; and subjecting the radiation at a point outside the selected portion of the patient's body to diffusive reflection by applying the radiation to a surface having diffuse reflection properties approaching those of a Lambertian surface so that generally uniform scattering of the radiation by the diffusively reflective surface predominates.

37. A method for non-invasively measuring the content or composition of one or more components within a tissue of a body portion, said method utilizing a pulsatory phenomenon and comprising the steps of:

emitting radiation having at least two wavelengths suitable for carrying out the measurement;

applying the radiation to a surface of a selected portion of the patient's body;

detecting radiation from a surface of the selected portion of the patient's body, the radiation evincing the pulsatile phenomenon and a property of the received radiation indicative of the chemical component;

providing a signal indicative of the chemical component content or composition; and subjecting the radiation at a point outside the selected portion of the patient's body to diffusive reflection by applying the radiation to a surface having diffuse reflection properties approaching those of a Lambertian surface so that generally uniform scattering of the radiation by the diffusively reflective surface predominates.

38. A method for non-invasively measuring the degree of oxygen saturation in a patient's blood, said method comprising the steps of:

emitting radiation having at least two wavelengths suitable for carrying out the measurement;

applying the radiation to a surface of a selected portion of the patient's body;

detecting radiation from a surface of the selected portion of the patient's body, the radiation evincing a property of the received radiation indicative of the degree of oxygen saturation in the patient's blood;

providing a signal indicative of the degree of oxygen saturation in the patient's blood; and subjecting the radiation at a point outside the selected portion of the patient's body to diffusive reflection by applying the radiation to a surface having diffuse reflection properties approaching those of a Lambertian surface so that generally uniform scattering of the radiation by the diffusively reflective surface predominates.

39. The method of claim 36, 37 or 38 further defined as subjecting the radiation to diffuse reflection at two points outside the selected portion of the patient's body by applying the radiation to a further surface having diffuse reflection properties approaching those of a Lambertian surface.

40. The method of claim 36, 37 or 38 further defined as applying the radiation to a first surface of the selected portion of the patient's body and as detecting radiation from a second surface of the selected position of the patient's body lying generally opposite said first surface.

41. The method of claim 36, 37 or 38 further defined as applying the radiation to, and detecting the radiation from, the same surface of the selected portion of the patient's body.

* * * * *